United States Patent
Suarez Saiz et al.

(10) Patent No.: US 10,165,945 B1
(45) Date of Patent: Jan. 1, 2019

(54) COGNITIVELY INTEGRATED INDICATING SYSTEM

(71) Applicant: International Business Machines Corporation, Armonk, NY (US)

(72) Inventors: Fernando J. Suarez Saiz, Armonk, NY (US); Masaaki Takamiya, Chapel Hill, NC (US); Vamshi Krishna Thotempudi, Chapel Hill, NC (US); Adrian P. Vrouwenvelder, Chapel Hill, NC (US)

(73) Assignee: International Business Machines Corporation, Armonk, NY (US)

( * ) Notice: Subject to any disclaimer, the term of this patent is extended or adjusted under 35 U.S.C. 154(b) by 0 days.

(21) Appl. No.: 15/689,110

(22) Filed: Aug. 29, 2017

(51) Int. Cl.
  *A61B 5/00* (2006.01)
  *G06F 19/00* (2018.01)
  *G06Q 50/22* (2018.01)

(52) U.S. Cl.
  CPC .......... *A61B 5/0015* (2013.01); *A61B 5/6804* (2013.01); *A61B 5/749* (2013.01); *A61B 5/7465* (2013.01); *G06F 19/3418* (2013.01); *G06Q 50/22* (2013.01)

(58) Field of Classification Search
  CPC .... A61B 5/0015; A61B 5/6804; A61B 5/7465
  USPC ................................... 340/870.07
  See application file for complete search history.

(56) References Cited

U.S. PATENT DOCUMENTS

| | | | |
|---|---|---|---|
| 4,718,124 A | 1/1988 | Sawicki et al. | |
| 4,837,863 A | 6/1989 | Van Scoy-Mosher | |
| 6,217,188 B1 | 4/2001 | Wainwright et al. | |
| 6,237,153 B1 * | 5/2001 | Bowens | A41D 13/1236 2/114 |
| 8,275,803 B2 | 9/2012 | Brown et al. | |
| 9,330,558 B2 * | 5/2016 | Logan | A41D 1/002 |

(Continued)

FOREIGN PATENT DOCUMENTS

CN  1948578 A  4/2007

OTHER PUBLICATIONS

"Project Jacquard", https://atap.google.com/jacquard/, downloaded from the internet on May 31, 2017, 33 pages.

(Continued)

*Primary Examiner* — Santiago Garcia
(74) *Attorney, Agent, or Firm* — Francis Lammes; Stephen J. Walder, Jr.; Damion Josephs

(57) ABSTRACT

A mechanism is provided for interactively indicating information associated with a patient on a hospital garment. A set of questions is identified utilizing a set of information received from a plurality of sources within a medical facility. The set of information is analyzed for a set of key elements. The set of key elements is utilized to identify one or more questions from a search question database. The one or more questions are submitted to a request processing pipeline implemented by a healthcare cognitive system. Responsive to receiving a response from the request processing pipeline, one or more communications are identified to be sent to one or more hospital garments associated with the patient and/or medical staff. The one or more communications are sent to the one or more hospital garments to cause the one or more hospital garments to change a visual cue.

20 Claims, 4 Drawing Sheets

(56) References Cited

U.S. PATENT DOCUMENTS

| | | | |
|---|---|---|---|
| 2002/0179094 A1* | 12/2002 | Perlow | A61B 90/39 |
| | | | 128/897 |
| 2003/0211797 A1 | 11/2003 | Hill et al. | |
| 2007/0067885 A1 | 3/2007 | Fernandez | |
| 2009/0178685 A1* | 7/2009 | Haines | A61B 5/411 |
| | | | 128/852 |
| 2009/0287678 A1 | 11/2009 | Brown et al. | |
| 2010/0050314 A1* | 3/2010 | Oleyar | A41D 13/1236 |
| | | | 2/83 |
| 2010/0100997 A1* | 4/2010 | Lee | H01R 13/2407 |
| | | | 2/69 |
| 2011/0066587 A1 | 3/2011 | Ferrucci et al. | |
| 2011/0107494 A1* | 5/2011 | Haines | A61B 5/411 |
| | | | 2/48 |
| 2011/0125734 A1 | 5/2011 | Duboue et al. | |
| 2012/0136231 A1* | 5/2012 | Markel | A61B 5/0015 |
| | | | 600/388 |
| 2012/0139828 A1* | 6/2012 | Lok | G09B 23/28 |
| | | | 345/156 |
| 2013/0007055 A1 | 1/2013 | Brown et al. | |
| 2013/0018652 A1 | 1/2013 | Ferrucci et al. | |
| 2013/0066886 A1 | 3/2013 | Bagchi et al. | |
| 2013/0248226 A1* | 9/2013 | Sime | A61B 5/04085 |
| | | | 174/251 |
| 2014/0070957 A1 | 3/2014 | Longinotti-Buitoni et al. | |
| 2015/0370320 A1* | 12/2015 | Connor | A61B 5/6831 |
| | | | 345/173 |
| 2016/0081405 A1* | 3/2016 | Gubitosa | A41D 13/1236 |
| | | | 2/114 |
| 2016/0179066 A1 | 6/2016 | Chadwick et al. | |
| 2016/0324460 A1* | 11/2016 | Kusens | A61B 5/447 |
| 2016/0338891 A1* | 11/2016 | Agdeppa | A61G 7/015 |
| 2017/0270250 A1* | 9/2017 | Dettman | G06F 19/322 |

OTHER PUBLICATIONS

"TeleTracking", http://www.teletracking.com/products/, downloaded from the internet Dec. 9, 2016, 4 pages.

Brusco, Sam, "Top 5 Medical Applications for Smart Fabric Technology", https://www.mdtmag.com/blog/2015/02/top-5-medical-applications-smart-fabric-technology, Feb. 26, 2015, 5 pages. Downloaded from the internet May 31, 2017.

Darell, Richard, "Smart Shirt Visually Morphs to Fit Your Every Endeavor", http://www.bitrebels.com/technology/plexus-smart-shirt-concept/, downloaded from the internet Dec. 9, 2016, 9 pages.

High, Rob, "The Era of Cognitive Systems: An Inside Look at IBM Watson and How it Works", IBM Corporation, Redbooks, Dec. 12, 2012, 16 pages.

McCord, M.C. et al., "Deep parsing in Watson", IBM J. Res. & Dev. vol. 56 No. 3/4 Paper 3, May/Jul. 2012, pp. 3:1-3:15.

Preus, Janet et al., "Innovators find a variety of markets for color-changing materials", http://specialtyfabricsreview.com/2016/09/01/innovators-find-a-variety-of-markets-for-color-changino-materials/, Sep. 1, 2016, 7 pages. Downloaded from the internet May 31, 2017.

Rubin, Ann, "Weaving Cognitive into Couture: Watson and Marchesa Collaborate for the Met Gala", https://www.ibm.com/blogs/think/2016/04/watson-and-marchesa/, Apr. 29, 2016, 16 pages. Downloaded from the internet Dec. 9, 2016.

Yuan, Michael J., "Waimn and healthcare, How natural language processing and semantic search could revolutionize clinical decision support", IBM Corporation, IBM developerWorks, http://www.ibm.com/developerworks/industry/library/ind-watson/, Apr. 12, 2011, 14 pages.

* cited by examiner

COGNITIVELY INTEGRATED INDICATING SYSTEM

BACKGROUND

The present application relates generally to an improved data processing apparatus and method and more specifically to mechanisms for interactively indicating information associated with a patient on a hospital garment worn by the patient and/or hospital staff using a cognitively integrated system.

With the increased usage of computing networks, such as the Internet, humans are currently inundated and overwhelmed with the amount of information available to them from various structured and unstructured sources. However, information gaps abound as users try to piece together what they can find that they believe to be relevant during searches for information on various subjects. To assist with such searches, recent research has been directed to generating Question and Answer (QA) systems which may take an input question, analyze it, and return results indicative of the most probable answer to the input question. QA systems provide automated mechanisms for searching through large sets of sources of content, e.g., electronic documents, and analyze them with regard to an input question to determine an answer to the question and a confidence measure as to how accurate an answer is for answering the input question.

Examples, of QA systems are Siri® from Apple®, Cortana® from Microsoft®, and question answering pipeline of the IBM Watson™ cognitive system available from International Business Machines (IBM®) Corporation of Armonk, N.Y. The IBM Watson™ system is an application of advanced natural language processing, information retrieval, knowledge representation and reasoning, and machine learning technologies to the field of open domain question answering. The IBM Watson™ system is built on IBM's DeepQA™ technology used for hypothesis generation, massive evidence gathering, analysis, and scoring. DeepQA™ takes an input question, analyzes it, decomposes the question into constituent parts, generates one or more hypothesis based on the decomposed question and results of a primary search of answer sources, performs hypothesis and evidence scoring based on a retrieval of evidence from evidence sources, performs synthesis of the one or more hypothesis, and based on trained models, performs a final merging and ranking to output an answer to the input question along with a confidence measure.

SUMMARY

This Summary is provided to introduce a selection of concepts in a simplified form that are further described herein in the Detailed Description. This Summary is not intended to identify key factors or essential features of the claimed subject matter, nor is it intended to be used to limit the scope of the claimed subject matter.

In one illustrative embodiment, a method, in a data processing system, is provided for interactively indicating information associated with a patient on a hospital garment. The illustrative embodiment identifies a set of questions utilizing a set of information received from a plurality of sources within a medical facility. The illustrative embodiment analyzes the set of information for a set of key elements. The illustrative embodiment utilizes the set of key elements to identify one or more questions from a search question database. The illustrative embodiment submits the one or more questions to a request processing pipeline implemented by a healthcare cognitive system. The illustrative embodiment identifies one or more communications to be sent to one or more hospital garments associated with the patient and/or medical staff in response to receiving a response from the request processing pipeline. The illustrative embodiment sends the one or more communications to the one or more hospital garments to cause the one or more hospital garments to change a visual cue.

In other illustrative embodiments, a computer program product comprising a computer useable or readable medium having a computer readable program is provided. The computer readable program, when executed on a computing device, causes the computing device to perform various ones of, and combinations of, the operations outlined above with regard to the method illustrative embodiment.

In yet another illustrative embodiment, a system/apparatus is provided. The system/apparatus may comprise one or more processors and a memory coupled to the one or more processors. The memory may comprise instructions which, when executed by the one or more processors, cause the one or more processors to perform various ones of, and combinations of, the operations outlined above with regard to the method illustrative embodiment.

These and other features and advantages of the present invention will be described in, or will become apparent to those of ordinary skill in the art in view of, the following detailed description of the example embodiments of the present invention.

BRIEF DESCRIPTION OF THE SEVERAL VIEWS OF THE DRAWINGS

The invention, as well as a preferred mode of use and further objectives and advantages thereof, will best be understood by reference to the following detailed description of illustrative embodiments when read in conjunction with the accompanying drawings, wherein.

DETAILED DESCRIPTION

Figure 1:
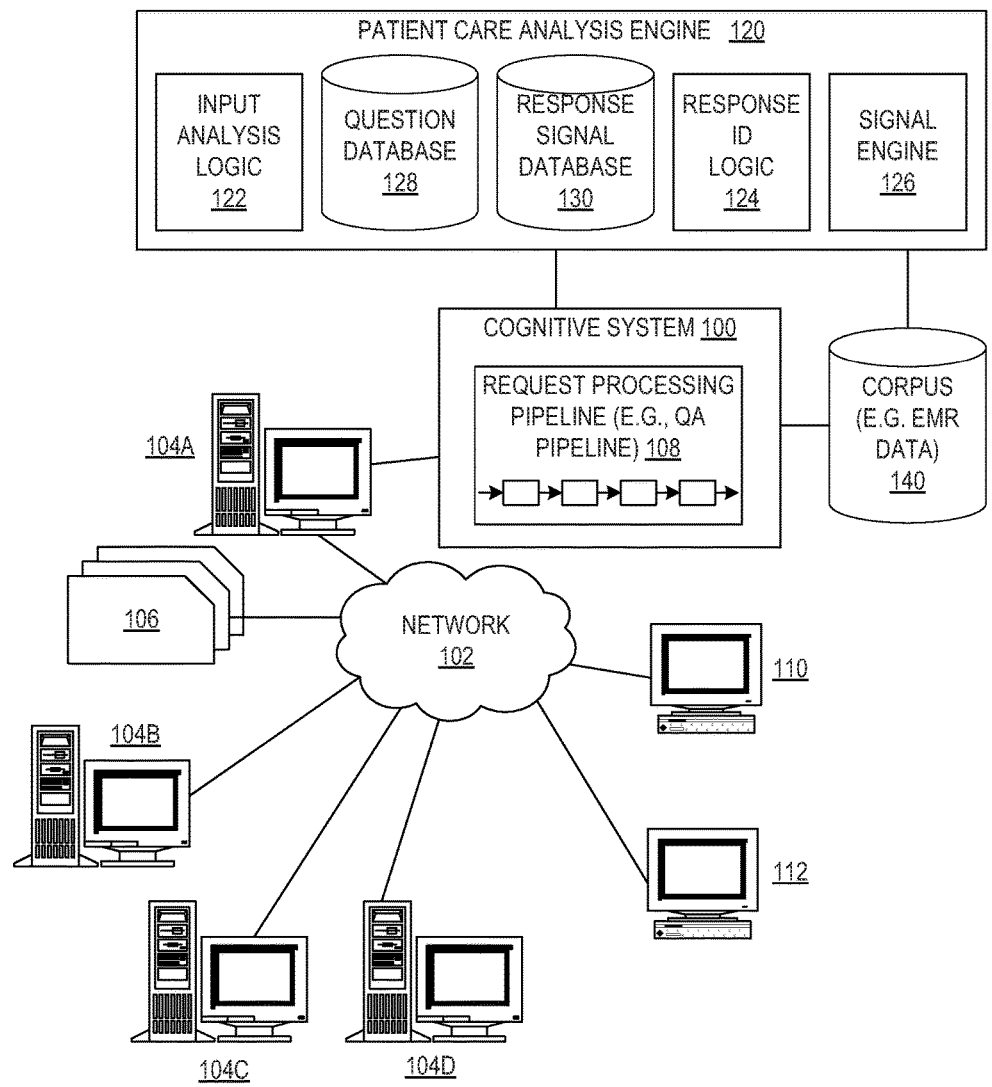
FIG. 1 depicts a schematic diagram of one illustrative embodiment of a cognitive system in a computer network.

The illustrative embodiments provide mechanisms for interactively indicating information associated with a patient on a hospital garment worn by the patient and/or hospital staff using a cognitively integrated system. In the healthcare industry, medical malpractice and medical negligence (hereafter referred to as "medical errors") are causing an alarming number of deaths each year. The U.S. Center for Disease Control (CDC) sets medical errors as the third most common cause of death in the US. Ten percent (10%) of all U.S. deaths are now due to medical errors. Medical errors are an under-recognized cause of death.

Examples of typical medical errors include, but are not limited to:

A doctor performs an appendectomy instead of a hysterectomy.

Replacing a healthy ACL on a patient's left knee instead of his right knee.

Giving the wrong medication or dose to a patient.

A patient may be sitting in a medical institution with a severe issue which is not immediately observable—e.g. severely high blood pressure, and that condition may be uploaded via a personal biometrics device to a system somewhere, but a medic at the institution is not made aware in a timely fashion.

Even with the existing technology (i.e. smart watches, bracelets, and other kinds of wearables), medical errors still happen much too frequently.

This invention helps solve the problem of medical errors by introducing interactive display capability to hospital garments. Integrated with a backend host and through obvious visual cues—such as changing colors and patterns—the hospital garments will ensure that the right patient is getting the right medical procedure or medicine at the right time, and that a doctor, surgeon, nurse, or other hospital staff is in the right place at the right time as well.

Before beginning the discussion of the various aspects of the illustrative embodiments in more detail, it should first be appreciated that throughout this description the term "mechanism" will be used to refer to elements of the present invention that perform various operations, functions, and the like. A "mechanism," as the term is used herein, may be an implementation of the functions or aspects of the illustrative embodiments in the form of an apparatus, a procedure, or a computer program product. In the case of a procedure, the procedure is implemented by one or more devices, apparatus, computers, data processing systems, or the like. In the case of a computer program product, the logic represented by computer code or instructions embodied in or on the computer program product is executed by one or more hardware devices in order to implement the functionality or perform the operations associated with the specific "mechanism." Thus, the mechanisms described herein may be implemented as specialized hardware, software executing on general purpose hardware, software instructions stored on a medium such that the instructions are readily executable by specialized or general purpose hardware, a procedure or method for executing the functions, or a combination of any of the above.

The present description and claims may make use of the terms "a," "at least one of," and "one or more of" with regard to particular features and elements of the illustrative embodiments. It should be appreciated that these terms and phrases are intended to state that there is at least one of the particular feature or element present in the particular illustrative embodiment, but that more than one can also be present. That is, these terms/phrases are not intended to limit the description or claims to a single feature/element being present or require that a plurality of such features/elements be present. To the contrary, these terms/phrases only require at least a single feature/element with the possibility of a plurality of such features/elements being within the scope of the description and claims.

Moreover, it should be appreciated that the use of the term "engine," if used herein with regard to describing embodiments and features of the invention, is not intended to be limiting of any particular implementation for accomplishing and/or performing the actions, steps, processes, etc., attributable to and/or performed by the engine. An engine may be, but is not limited to, software, hardware and/or firmware or any combination thereof that performs the specified functions including, but not limited to, any use of a general and/or specialized processor in combination with appropriate software loaded or stored in a machine readable memory and executed by the processor. Further, any name associated with a particular engine is, unless otherwise specified, for purposes of convenience of reference and not intended to be limiting to a specific implementation. Additionally, any functionality attributed to an engine may be equally performed by multiple engines, incorporated into and/or combined with the functionality of another engine of the same or different type, or distributed across one or more engines of various configurations.

In addition, it should be appreciated that the following description uses a plurality of various examples for various elements of the illustrative embodiments to further illustrate example implementations of the illustrative embodiments and to aid in the understanding of the mechanisms of the illustrative embodiments. These examples intended to be non-limiting and are not exhaustive of the various possibilities for implementing the mechanisms of the illustrative embodiments. It will be apparent to those of ordinary skill in the art in view of the present description that there are many other alternative implementations for these various elements that may be utilized in addition to, or in replacement of, the examples provided herein without departing from the spirit and scope of the present invention.

As noted above, the present invention provides mechanisms for interactively indicating information associated with a patient on a hospital garment worn by the patient using a cognitively integrated system. In one embodiment, patients and staff wear interactive garments, such as hospital gowns, scrubs, uniforms, or the like, which are able to change color and patterns based on a wireless signal from a server. Utilizing information obtained about the patient, such as sensed biometric information, information from the patient's electronic medical records (EMR), location information associated with the patient and staff, identity information associated with the staff, and the like, a healthcare cognitive system is able to analyze the information and alert the patient and/or staff of information pertinent to the patient.

As one example, when a nurse enters a patient's room in order to administer penicillin to the patient and the nurse scans the penicillin prior to the administration, the healthcare cognitive system utilizes the scanning of the penicillin as an indication to analyze the patient's EMR for any reason that the penicillin cannot be administered. If in scanning the patient's EMR, the healthcare cognitive system determines that the patient is allergic to penicillin or the administration of the penicillin is not part of the doctor's orders, the healthcare cognitive system sends a signal to the garment worn by the patient that causes all or a portion of the garment to turn a color, such as, for example, red, thereby providing an indication to the nurse that the penicillin should not be administered to the patient. Alternatively, if in scanning the patient's EMR, the healthcare cognitive system determines that the patient is not allergic to penicillin and the administration of the penicillin is part of the doctor's orders, the healthcare cognitive system sends a signal to the garment worn by the patient that causes all or a portion of the garment to turn a different color, such as, for example, green, thereby providing an indication to the nurse that the penicillin may be administered to the patient. Utilizing this type of information, the healthcare cognitive system reduces the likelihood of a patient receiving incorrect medication that may be harmful to the patient.

As another example, when a doctor or surgeon enters a patient's room prior to surgery, the healthcare cognitive system detects the entry via radio-frequency identification (RFID), Indoor Positioning Sensing (IPS), or the like, from a signal received from the doctor's or surgeon's garment, identification card, or the like. The healthcare cognitive system utilizes the identified entry as an indication to analyze the patient's EMR and identify a location on the patients' body where the surgery is to occur as well as where any previous surgery/surgeries has/have occurred. Responsive to identifying a location of where the surgery is to occur as well as where previous surgery/surgeries has/have occurred, the healthcare cognitive system sends a signal to the garment worn by the patient that causes a portion of the garment where the surgery is to occur to turn a color, such as, for example, green, and locations while turning other portions of the garment where previous surgery/surgeries has/have occurred to turn a color, such as, for example, blue, thereby providing information to the doctor or surgeon of a location on the patient's body where the surgery is to occur and reducing the likelihood of an erroneous surgery taking place.

In addition to the previous example, if a doctor or surgeon incorrectly enters a patient's room who is not a patient of the doctor or surgeon, the healthcare cognitive system detects the entry via radio-frequency identification (RFID), Indoor Positioning Sensing (IPS), or the like, from a signal received from the doctor's or surgeon's garment, identification card, or the like. The healthcare cognitive system utilizes the identified entry as an indication to analyze the patient's EMR and identify whether the doctor or surgeon is associated with the patient. Responsive to identifying that the doctor or surgeon fails to be associated with the patient, the healthcare cognitive system sends a signal to the garment worn by the patient that that causes all or a portion of the garment to turn a color, such as, for example, red, thereby providing an indication to the doctor or surgeon that the patient is not their patient.

Figure 2:
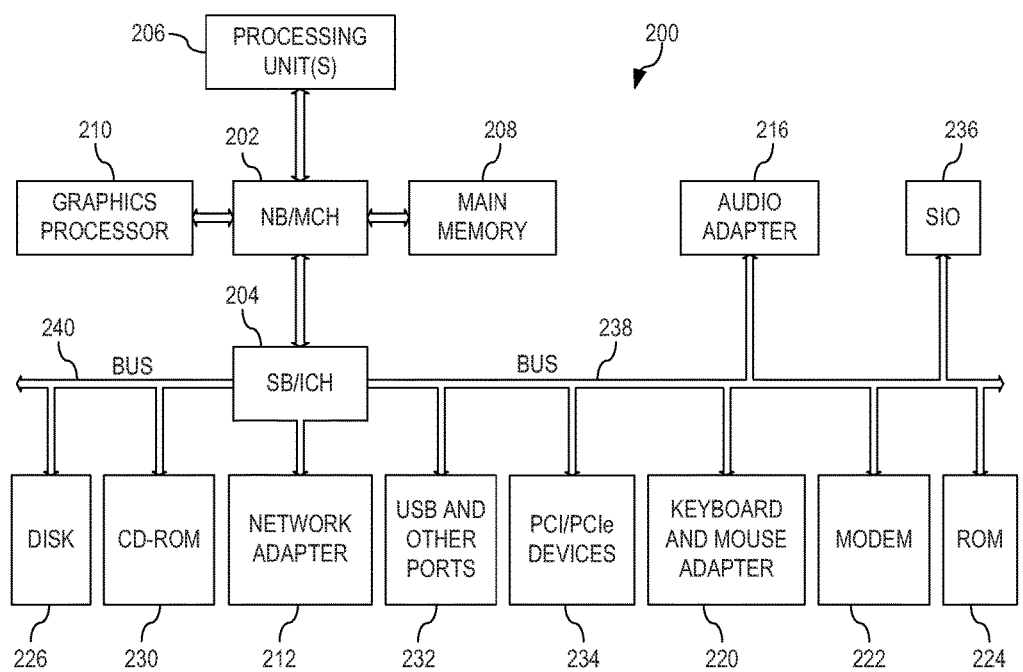
FIG. 2 is a block diagram of an example data processing system in which aspects of the illustrative embodiments are implemented.
Figure 3:
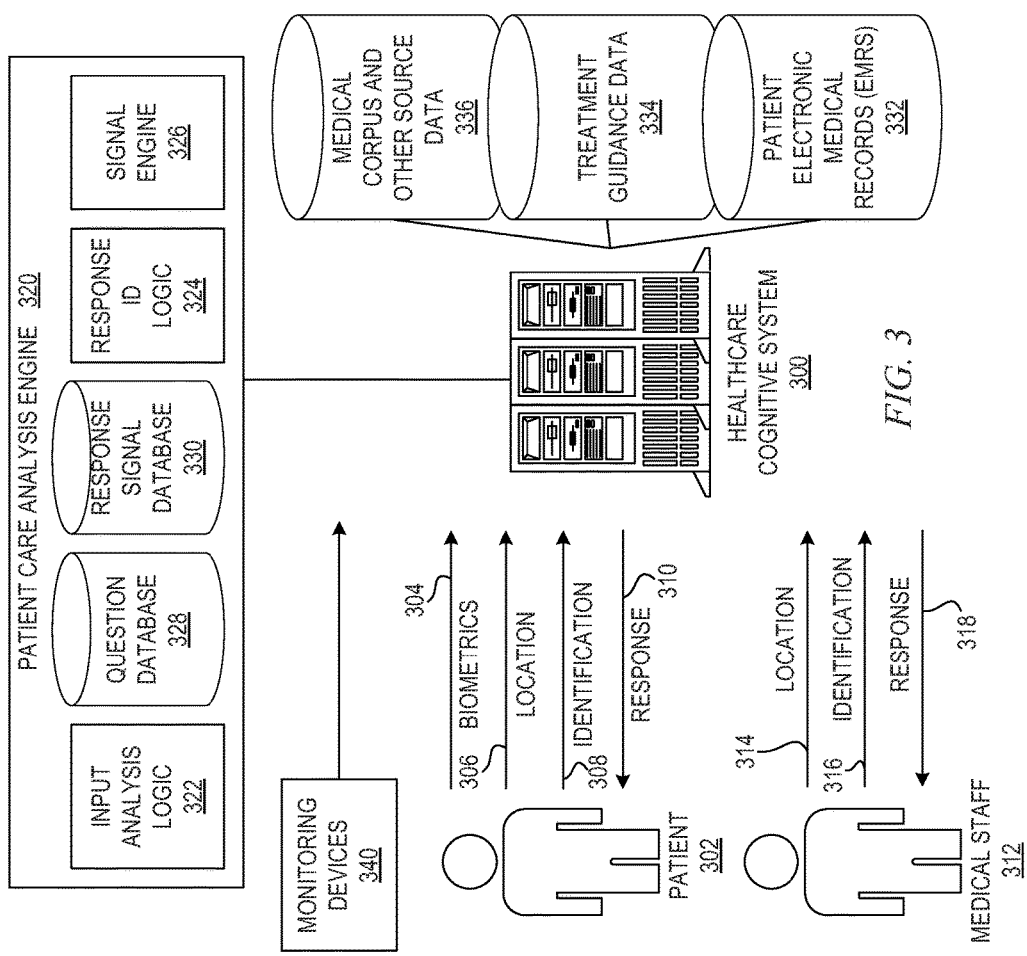
FIG. 3 is an example diagram illustrating an interaction of elements of a healthcare cognitive system in accordance with one illustrative embodiment.

Thus, the illustrative embodiments may be utilized in many different types of data processing environments. In order to provide a context for the description of the specific elements and functionality of the illustrative embodiments, FIGS. 1-3 are provided hereafter as example environments in which aspects of the illustrative embodiments may be implemented. It should be appreciated that FIGS. 1-3 are only examples and are not intended to assert or imply any limitation with regard to the environments in which aspects or embodiments of the present invention may be implemented. Many modifications to the depicted environments may be made without departing from the spirit and scope of the present invention.

FIGS. 1-3 are directed to describing an example cognitive system for interactively indicating information associated with a patient on a hospital garment worn by the patient and/or hospital staff which implements a request processing pipeline, such as a Question Answering (QA) pipeline (also referred to as a Question/Answer pipeline or Question and Answer pipeline) for example, request processing methodology, and request processing computer program product with which the mechanisms of the illustrative embodiments are implemented. These requests may be provided as structure or unstructured request messages, natural language questions, or any other suitable format for requesting an operation to be performed by the cognitive system. As described in more detail hereafter, the particular application that is implemented in the cognitive system of the present invention is an application for interactively indicating information associated with a patient on a hospital garment worn by the patient and/or hospital staff.

It should be appreciated that the cognitive system, while shown as having a single request processing pipeline in the examples hereafter, may in fact have multiple request processing pipelines. Each request processing pipeline may be separately trained and/or configured to process requests associated with different domains or be configured to perform the same or different analysis on input requests (or questions in implementations using a QA pipeline), depending on the desired implementation. For example, in some cases, a first request processing pipeline may be trained to operate on input requests directed to mediation to be administered to a patient. If a scanned medication is a medication to which the patient is allergic or the administration of the medication is not part of the doctor's orders, the cognitive system sends a signal to the garment worn by the patient that causes all or a portion of the garment to turn a color, such as, for example, red, thereby providing an indication that the medication should not be administered to the patient. In other cases, for example, the request processing pipelines may be configured to provide different types of cognitive functions or support different types of applications, such as one request processing pipeline being used for input requests directed to indicating whether doctor or surgeon is an attending physician of the patient. If a doctor or surgeon enters a patient's room and is not an attending physician, the cognitive system sends a signal to the garment worn by the patient that causes all or a portion of the garment to turn a color, such as, for example, red, thereby providing an indication to the doctor or surgeon that this patient is not their patient.

Moreover, each request processing pipeline may have its own associated corpus or corpora that they ingest and operate on, e.g., one corpus for patient electronic medical records (EMRs), another corpus for doctors, surgeons, nurses, therapists, or the like, and yet another corpus for medications related documents in the above examples. In some cases, the request processing pipelines may each operate on the same domain of input questions but may have different configurations, e.g., different annotators or differently trained annotators, such that different analysis and potential answers are generated. The cognitive system may provide additional logic for routing input questions to the appropriate request processing pipeline, such as based on a determined domain of the input request, combining and evaluating final results generated by the processing performed by multiple request processing pipelines, and other control and interaction logic that facilitates the utilization of multiple request processing pipelines.

As noted above, one type of request processing pipeline with which the mechanisms of the illustrative embodiments may be utilized is a Question Answering (QA) pipeline. The description of example embodiments of the present invention hereafter will utilize a QA pipeline as an example of a request processing pipeline that may be augmented to include mechanisms in accordance with one or more illustrative embodiments. It should be appreciated that while the present invention will be described in the context of the cognitive system implementing one or more QA pipelines that operate on an input question, the illustrative embodiments are not limited to such. Rather, the mechanisms of the illustrative embodiments may operate on requests that are not posed as "questions" but are formatted as requests for the cognitive system to perform cognitive operations on a specified set of input data using the associated corpus or corpora and the specific configuration information used to configure the cognitive system. For example, rather than asking a natural language question of "What diagnosis applies to patient P?", the cognitive system may instead receive a request of "verify whether a particular medication may be given to patient P," or the like. It should be appreciated that the mechanisms of the QA system pipeline may operate on requests in a similar manner to that of input natural language questions with minor modifications. In fact, in some cases, a request may be converted to a natural language question for processing by the QA system pipelines if desired for the particular implementation.

As will be discussed in greater detail hereafter, the illustrative embodiments may be integrated in, augment, and extend the functionality of these QA pipeline, or request processing pipeline, mechanisms of a healthcare cognitive system with regard to interactively indicating information associated with a patient on a hospital garment worn by the patient and/or hospital staff.

Thus, it is important to first have an understanding of how cognitive systems and question and answer creation in a cognitive system implementing a QA pipeline is implemented before describing how the mechanisms of the illustrative embodiments are integrated in and augment such cognitive systems and request processing pipeline, or QA pipeline, mechanisms. It should be appreciated that the mechanisms described in FIGS. 1-3 are only examples and are not intended to state or imply any limitation with regard to the type of cognitive system mechanisms with which the illustrative embodiments are implemented. Many modifications to the example cognitive system shown in FIGS. 1-3 may be implemented in various embodiments of the present invention without departing from the spirit and scope of the present invention.

As an overview, a cognitive system is a specialized computer system, or set of computer systems, configured with hardware and/or software logic (in combination with hardware logic upon which the software executes) to emulate human cognitive functions. These cognitive systems apply human-like characteristics to conveying and manipulating ideas which, when combined with the inherent strengths of digital computing, can solve problems with high accuracy and resilience on a large scale. A cognitive system performs one or more computer-implemented cognitive operations that approximate a human thought process as well as enable people and machines to interact in a more natural manner so as to extend and magnify human expertise and cognition. A cognitive system comprises artificial intelligence logic, such as natural language processing (NLP) based logic, for example, and machine learning logic, which may be provided as specialized hardware, software executed on hardware, or any combination of specialized hardware and software executed on hardware. The logic of the cognitive system implements the cognitive operation(s), examples of which include, but are not limited to, question answering, identification of related concepts within different portions of content in a corpus, intelligent search algorithms, such as Internet web page searches, for example, medical diagnostic and treatment recommendations, and other types of recommendation generation, e.g., items of interest to a particular user, potential new contact recommendations, or the like.

IBM Watson™ is an example of one such cognitive system which can process human readable language and identify inferences between text passages with human-like high accuracy at speeds far faster than human beings and on a larger scale. In general, such cognitive systems are able to perform the following functions:

Navigate the complexities of human language and understanding

Ingest and process vast amounts of structured and unstructured data

Generate and evaluate hypothesis

Weigh and evaluate responses that are based only on relevant evidence

Provide situation-specific advice, insights, and guidance

Improve knowledge and learn with each iteration and interaction through machine learning processes Enable decision making at the point of impact (contextual guidance)

Scale in proportion to the task

Extend and magnify human expertise and cognition

Identify resonating, human-like attributes and traits from natural language

Deduce various language specific or agnostic attributes from natural language

High degree of relevant recollection from data points (images, text, voice) (memorization and recall)

Predict and sense with situational awareness that mimic human cognition based on experiences Answer questions based on natural language and specific evidence Initiate outputs to other devices base on determined details In one aspect, cognitive systems provide mechanisms for answering or responding to questions or input posed to these cognitive systems using a Question Answering pipeline or system (QA system) and/or process requests which may or may not be posed as natural language questions. The QA pipeline or system is an artificial intelligence application executing on data processing hardware that answers or responds to input pertaining to a given subject-matter domain presented in natural language. The QA pipeline receives inputs from various sources including input over a network, a corpus of electronic documents or other data, data from a content creator, information from one or more content users, and other such inputs from other possible sources of input. Data storage devices store the corpus of data. A content creator creates content in a document for use as part of a corpus of data with the QA pipeline. The document may include any file, text, article, or source of data for use in the QA system. For example, a QA pipeline accesses a body of knowledge about the domain, or subject matter area, e.g., financial domain, medical domain, legal domain, etc., where the body of knowledge (knowledgebase) can be organized in a variety of configurations, e.g., a structured repository of domain-specific information, such as ontologies, or unstructured data related to the domain, or a collection of natural language documents about the domain.

Content users input questions and/or information to cognitive system which implements the QA pipeline. The QA pipeline then determines answers or appropriate responses using the content in the corpus of data by evaluating documents, sections of documents, portions of data in the corpus, or the like. When a process evaluates a given section of a document for semantic content, the process can use a variety of conventions to query such document from the QA pipeline, e.g., sending the query to the QA pipeline as a well-formed question which is then interpreted by the QA pipeline and a response is provided to the input. Semantic content is content based on the relation between signifiers, such as words, phrases, signs, and symbols, and what they stand for, their denotation, or connotation. In other words, semantic content is content that interprets an expression, such as by using Natural Language Processing.

As will be described in greater detail hereafter, the QA pipeline receives input, parses the input to extract the major features of the input, uses the extracted features to formulate queries, and then applies those queries to the corpus of data. Based on the application of the queries to the corpus of data, the QA pipeline generates a set of hypotheses, or candidate answers or responses to the input, by looking across the corpus of data for portions of the corpus of data that have some potential for containing a valuable response to the input. The QA pipeline then performs deep analysis on the language of the input and the language used in each of the portions of the corpus of data found during the application of the queries using a variety of reasoning algorithms. There may be hundreds or even thousands of reasoning algorithms applied, each of which performs different analysis, e.g., comparisons, natural language analysis, lexical analysis, or the like, and generates a score. For example, some reasoning algorithms may look at the matching of terms and synonyms within the language of the input and the found portions of the corpus of data. Other reasoning algorithms may look at temporal or spatial features in the language, while others may evaluate the source of the portion of the corpus of data and evaluate its veracity.

The scores obtained from the various reasoning algorithms indicate the extent to which the potential response is inferred by the input based on the specific area of focus of that reasoning algorithm. Each resulting score is then weighted against a statistical model. The statistical model captures how well the reasoning algorithm performed at establishing the inference between two similar passages for a particular domain during the training period of the QA pipeline. The statistical model is used to summarize a level of confidence that the QA pipeline has regarding the evidence that the potential response is inferred by the input. This process is repeated for each of the responses until the QA pipeline identifies one or more responses that surface as being significantly stronger than others and thus, generates a final response, or ranked set of responses, for the input.

As mentioned above, QA pipeline mechanisms operate by accessing information from a corpus of data or information (also referred to as a corpus of content), analyzing it, and then generating responses results based on the analysis of this data. Accessing information from a corpus of data typically includes: a database query that responds to input about what is in a collection of structured records, and a search that delivers a collection of document links in response to a query against a collection of unstructured data (text, markup language, etc.). Conventional QA systems are capable of generating responses based on the corpus of data and the input, verifying responses to a collection of input for the corpus of data, correcting errors in digital text using a corpus of data, and selecting one or more responses to the input from a pool of potential responses.

Content creators, such as article authors, electronic document creators, web page authors, document database creators, and the like, determine use cases for products, solutions, and services described in such content before writing their content. Consequently, the content creators know what input the content is intended to respond in a particular topic addressed by the content. Categorizing the input, such as in terms of roles, type of information, tasks, or the like, associated with the input, in each document of a corpus of data allows the QA pipeline to more quickly and efficiently identify documents containing content related to a specific query. The content may also respond to other input that the content creator did not contemplate that may be useful to content users. The input and responses may be verified by the content creator to be contained in the content for a given document. These capabilities contribute to improved accuracy, system performance, machine learning, and confidence of the QA pipeline. Content creators, automated tools, or the like, annotate or otherwise generate metadata for providing information useable by the QA pipeline to identify these input and response attributes of the content.

Operating on such content, the QA pipeline generates answers or responses for input using a plurality of intensive analysis mechanisms which evaluate the content to identify the most probable answers or responses for the input. The most probable responses are output as a ranked listing of candidate responses ranked according to their relative scores or confidence measures calculated during evaluation of the candidate responses, as a single final response having a highest ranking score or confidence measure, or which is a best match to the input, or a combination of ranked listing and final answer or response.

FIG. 1 depicts a schematic diagram of one illustrative embodiment of a cognitive system 100 implementing a request processing pipeline 108, which in some embodiments may be a question answering (QA) pipeline, in a computer network 102. For purposes of the present description, it will be assumed that the request processing pipeline 108 is implemented as a QA pipeline that operates on structured and/or unstructured requests in the form of input information, questions, or the like. One example of a question processing operation which may be used in conjunction with the principles described herein is described in U.S. Patent Application Publication No. 2011/0125734, which is herein incorporated by reference in its entirety. The cognitive system 100 is implemented on one or more computing devices 104A-D (comprising one or more processors and one or more memories, and potentially any other computing device elements generally known in the art including buses, storage devices, communication interfaces, and the like) connected to the computer network 102. For purposes of illustration only, FIG. 1 depicts the cognitive system 100 being implemented on computing device 104A only, but as noted above the cognitive system 100 may be distributed across multiple computing devices, such as a plurality of computing devices 104A-D. The network 102 includes multiple computing devices 104A-D, which may operate as server computing devices, and 110-112 which may operate as client computing devices, in communication with each other and with other devices or components via one or more wired and/or wireless data communication links, where each communication link comprises one or more of wires, routers, switches, transmitters, receivers, or the like. In some illustrative embodiments, the cognitive system 100 and network 102 enables question processing and answer generation (QA) functionality for one or more cognitive system users via their respective computing devices 110-112. In other embodiments, the cognitive system 100 and network 102 may provide other types of cognitive operations including, but not limited to, request processing and cognitive response generation which may take many different forms depending upon the desired implementation, e.g., cognitive information retrieval, training/instruction of users, cognitive evaluation of data, or the like. Other embodiments of the cognitive system 100 may be used with components, systems, sub-systems, and/or devices other than those that are depicted herein.

The cognitive system 100 is configured to implement a request processing pipeline 108 that receive inputs from various sources. The requests may be posed in the form of a natural language question, natural language request for information, natural language request for the performance of a cognitive operation, or the like. For example, the cognitive system 100 receives input from the network 102, a corpus or corpora of electronic documents 106, cognitive system users, and/or other data and other possible sources of input, such as, in accordance with the illustrative embodiments, scanners, location detectors, hospital garments worn by the patient and/or hospital staff, inventory systems, or the like. In one embodiment, some or all of the inputs to the cognitive system 100 are routed through the network 102. The various computing devices 104A-D on the network 102 include access points for content creators and cognitive system users. Some of the computing devices 104A-D include devices for a database storing the corpus or corpora of data 106 (which is shown as a separate entity in FIG. 1 for illustrative purposes only). Portions of the corpus or corpora of data 106 may also be provided on one or more other network attached storage devices, in one or more databases, or other computing devices not explicitly shown in FIG. 1. The network 102 includes local network connections and remote connections in various embodiments, such that the cognitive system 100 may operate in environments of any size, including local and global, e.g., the Internet.

In one embodiment, the content creator creates content in a document of the corpus or corpora of data 106 for use as part of a corpus of data with the cognitive system 100. The document includes any file, text, article, or source of data for use in the cognitive system 100. Cognitive system users access the cognitive system 100 via a network connection or an Internet connection to the network 102, and input questions/requests to the cognitive system 100 that are answered/processed based on the content in the corpus or corpora of data 106. In one embodiment, the questions/requests are formed using natural language. The cognitive system 100 parses and interprets the question/request via request processing pipeline 108, and provides a response to the cognitive system user, e.g., cognitive system user 110, containing one or more answers to the question posed, response to the request, results of processing the request, or the like. In some embodiments, the cognitive system 100 provides a response to users in a ranked list of candidate answers/responses while in other illustrative embodiments, the cognitive system 100 provides a single final answer/response or a combination of a final answer/response and ranked listing of other candidate answers/responses.

The cognitive system 100 implements request processing pipeline 108 which comprises a plurality of stages for processing an input question/request based on information obtained from the corpus or corpora of data 106. Request processing pipeline 108 generates answers/responses for the input question or request based on the processing of the input question/request and the corpus or corpora of data 106. In some illustrative embodiments, the cognitive system 100 may be the IBM Watson™ cognitive system available from International Business Machines Corporation of Armonk, N.Y., which is augmented with the mechanisms of the illustrative embodiments described hereafter. As outlined previously, a pipeline of the IBM Watson™ cognitive system receives an input question or request which it then parses to extract the major features of the question/request, which in turn are then used to formulate queries that are applied to the corpus or corpora of data 106. Based on the application of the queries to the corpus or corpora of data 106, a set of hypotheses, or candidate answers/responses to the input question/request, are generated by looking across the corpus or corpora of data 106 for portions of the corpus or corpora of data 106 (hereafter referred to simply as the corpus 106) that have some potential for containing a valuable response to the input question/response (hereafter assumed to be an input question). Request processing pipeline 108 of the IBM Watson™ cognitive system then performs deep analysis on the language of the input question and the language used in each of the portions of the corpus 106 found during the application of the queries using a variety of reasoning algorithms.

The scores obtained from the various reasoning algorithms are then weighted against a statistical model that summarizes a level of confidence that request processing pipeline 108 of the IBM Watson™ cognitive system 100, in this example, has regarding the evidence that the potential candidate answer is inferred by the question. This process is be repeated for each of the candidate answers to generate ranked listing of candidate answers which may then be presented to the user that submitted the input question, e.g., a user of client computing device 110, or from which a final answer is selected and presented to the user. More information about request processing pipeline 108 of the IBM Watson™ cognitive system 100 may be obtained, for example, from the IBM Corporation website, IBM Redbooks, and the like. For example, information about the pipeline of the IBM Watson™ cognitive system can be found in Yuan et al., "Watson and Healthcare," IBM developerWorks, 2011 and "The Era of Cognitive Systems: An Inside Look at IBM Watson and How it Works" by Rob High, IBM Redbooks, 2012.

As noted above, while the input to the cognitive system 100 from a client device may be posed in the form of a natural language question, the illustrative embodiments are not limited to such. Rather, the input question may in fact be formatted or structured as any suitable type of request which may be parsed and analyzed using structured and/or unstructured input analysis, including but not limited to the natural language parsing and analysis mechanisms of a cognitive system such as IBM Watson™, to determine the basis upon which to perform cognitive analysis and providing a result of the cognitive analysis. In the case of a healthcare based cognitive system, this analysis may involve processing patient medical records, medical guidance documentation from one or more corpora, and the like, to provide a healthcare oriented cognitive system result.

In the context of the present invention, cognitive system 100 may provide a cognitive functionality for interactively indicating information associated with a patient on a hospital garment worn by the patient and/or hospital staff. For example, depending upon the particular implementation, the healthcare cognitive system based operations may comprise patient diagnostics, medical treatment recommendation systems, medical practice management systems, personal patient care plan generation and monitoring, patient electronic medical record (EMR) evaluation for various purposes, such as for identifying patients that are suitable for a medical trial or a particular type of medical treatment, or the like. Thus, the cognitive system 100 may be a healthcare cognitive system 100 that operates in the medical or healthcare type domains and which may process requests for such healthcare operations via the request processing pipeline 108 input as either structured or unstructured requests, natural language input questions, or the like. In one illustrative embodiment, the cognitive system 100 is a healthcare cognitive system for interactively indicating information associated with a patient on a hospital garment worn by the patient. In one embodiment, patients and staff wear interactive garments, such as hospital gowns, scrubs, uniforms, or the like, which are able to change a visual cue, such as color and patterns, based on a wireless signal from a server. Utilizing information obtained about the patient, such as sensed biometric information, information from the patient's electronic medical records (EMR), location information associated with the patient and medical staff, identity information associated with the staff, and the like, a healthcare cognitive system is able to analyze the information and alert the patient and/or staff of information pertinent to the patient.

As shown in FIG. 1, the cognitive system 100 is further augmented, in accordance with the mechanisms of the illustrative embodiments, to include logic implemented in specialized hardware, software executed on hardware, or any combination of specialized hardware and software executed on hardware, for implementing patient care analysis engine 120 that interactively indicates information associated with a patient on a hospital garment worn by the patient. Patient care analysis engine 120 receives input from a plurality of devices such as, for example:

Biometric information associated with a patient.
Scanner, digital reader, or the like, that scans medication, medical devices, or the like, when being pulled from inventory in order to be administered to the patient.
Scanner, digital reader, or the like, that scans medication, medical devices, or the like, prior to being administered to the patient.
Location monitors that identify patient and medical staff location throughout the facility of which the patient is a visitor.
Information from the patient's electronic medical records (EMR) including, but not limited to, a patient's medical history, doctor's orders for the patient, or the like.
Medical information associated with diseases, drug interactions, or the like.

As shown in FIG. 1, patient care analysis engine 120 comprises input analysis logic 122, response identification logic 124, and signaling engine 126. Upon receiving the input from the plurality of device, input analysis logic 122 analyzes the input for key elements for use in identifying one or more questions to pose to request processing pipeline 108. For example, if the input is a scan of barcode associated with Patient A's identification tag and a scan of a barcode of a medicine that is to be administered to Patient A, then input analysis logic 122 may search question database 128 for one or more questions related to both a barcode of a patient and a barcode of a medicine identifying, for example, questions such as "Do the electronic medical records of patient [A] indicate that medicine [X] is to be administered?", "Do the electronic medical records of patient [A] indicate that patient [A] is allergic to medicine [X]?", "Does medicine [X] have any adverse reactions to other medicines administered to patient [A]?, or the like. Responsive to input analysis logic 122 identifying an existence of one or more questions from question database 128 that are associated with a barcode of a patient and a barcode of a medicine, input analysis logic 122 sends the one or more questions to request processing pipeline 108.

Request processing pipeline 108 parses and interprets the question/request and provides a response to patient care analysis engine 120. That is, request processing pipeline 108 comprises a plurality of stages for processing an input question/request based on information obtained from the corpus or corpora of data 106. Request processing pipeline 108 generates answers/responses for the input question or request based on the processing of the input question/request and the corpus or corpora of data 106. Based on the application of the queries to the corpus or corpora of data 106, a set of hypotheses, or candidate answers/responses to the input question/request, are generated by looking across the corpus or corpora of data 106 for portions of the corpus or corpora of data 106 (hereafter referred to simply as the corpus 106) that have some potential for containing a valuable response to the input question/response (hereafter assumed to be an input question). Request processing pipeline 108 then performs deep analysis on the language of the input question and the language used in each of the portions of the corpus 106 found during the application of the queries using a variety of reasoning algorithms. The scores obtained from the various reasoning algorithms are then weighted against a statistical model that summarizes a level of confidence that request processing pipeline 108 has regarding the evidence that the potential candidate answer is inferred by the question. This process is be repeated for each of the candidate answers to generate ranked listing of candidate answers which may then be presented to patient care analysis engine 120.

Upon receiving the candidate answers from request processing pipeline 108, response identification logic 124 utilizes the submitted question from input analysis logic 122 and the response from request processing pipeline 108 to identify an appropriate response to initiate from response signal database 130. For example, if the posed question is "Do the electronic medical records of patient [A] indicate that medicine [X] is to be administered?" and the response is "No", then response identification logic 124 may identify that an appropriate response signal is to change a visual cue of all or a portion of the hospital garment worn by Patient A to a first color, such as red. Alternatively, if the posed question is "Do the electronic medical records of patient [A] indicate that medicine [X] is to be administered?" and the response is "Yes", then response identification logic 124 may identify that an appropriate response signal is to change a visual cue of all or a portion of the hospital garment worn by Patient A to a second color, such as green. If two or more questions are posed to request processing pipeline 108 and if any of the answers indicate that a medical error may be cause by the administration of the medicine to Patient A, then response identification logic 124 may utilize the most negative signal as the signal to be initiated. For example, if the electronic medical records indicate that penicillin is to be administered to Patient A but the electronic medical records also indicate that Patient A is allergic to penicillin, then response identification logic 124 would use the allergy of Patient A to penicillin as an overriding factor and identify that an appropriate response signal is to change a visual cue of all or a portion of the hospital garment worn by Patient A to a first color, such as red.

Once response identification logic 124 has identified an appropriate signal to be sent to the hospital garment worn by Patient A, response identification logic 124 sends the identified signal to signal engine 126. Signal engine 126 then sends a communication to one or more hospital garments associated with the patient and/or medical staff to indicate that a medical error may be forthcoming thereby causing the medical staff to verify the current procedure. That is, in keeping with the current example, if a nurse scans of barcode associated with Patient A's identification tag and scans of a barcode of a medicine that is to be administered to Patient A and patient care analysis engine 120 in association with request processing pipeline 108 identify that the medicine should not be administered to Patient A thereby turning a visual cue of the hospital garment of Patient A to red. The change of the visual cue of the hospital garment would be an indication to the nurse that the medicine should not be administered to Patient A.

The above description exemplifies one embodiment where the patient's hospital garment changes a visual cue of the hospital garment to a different color or pattern. However, a similar process may be implemented for the garments worn by the hospital staff. For example, prior to administering a medication to Patient A, the nurse acquires the medicine from hospital inventor. As hospitals keep track of which medicine is administered to which patient for billing purposes, as the nurse obtains the medicine from inventory, the nurse has to associate a patient identifier with the inventory withdrawal. Thus, when the nurse enters the patient identifier and then medicine to be withdrawn from inventory, patient care analysis engine 120 may operate as describe previously. That is, if a nurse enters Patient A's identification and the medicine that is to be administered to Patient A and patient care analysis engine 120 in association with request processing pipeline 108 may identify that the medicine should not be administered to Patient A thereby turning the hospital garment of nurse to red thereby providing an indication to the nurse that the medicine should not be administered to Patient A. Patient care analysis engine 120 may also prevent then medicine from being pulled from inventory until the identification of the possible medical error has been addressed, thereby reducing patient billing errors.

As noted above, the mechanisms of the illustrative embodiments are rooted in the computer technology arts and are implemented using logic present in such computing or data processing systems. These computing or data processing systems are specifically configured, either through hardware, software, or a combination of hardware and software, to implement the various operations described above. As such, FIG. 2 is provided as an example of one type of data processing system in which aspects of the present invention may be implemented. Many other types of data processing systems may be likewise configured to specifically implement the mechanisms of the illustrative embodiments.

FIG. 2 is a block diagram of an example data processing system in which aspects of the illustrative embodiments are implemented. Data processing system 200 is an example of a computer, such as server 104 or client 110 in FIG. 1, in which computer usable code or instructions implementing the processes for illustrative embodiments of the present invention are located. In one illustrative embodiment, FIG. 2 represents a server computing device, such as a server 104, which, which implements a cognitive system 100 and request processing pipeline 108 augmented to include the additional mechanisms of the illustrative embodiments described hereafter.

In the depicted example, data processing system 200 employs a hub architecture including north bridge and memory controller hub (NB/MCH) 202 and south bridge and input/output (I/O) controller hub (SB/ICH) 204. Processing unit 206, main memory 208, and graphics processor 210 are connected to NB/MCH 202. Graphics processor 210 is connected to NB/MCH 202 through an accelerated graphics port (AGP).

In the depicted example, local area network (LAN) adapter 212 connects to SB/ICH 204. Audio adapter 216, keyboard and mouse adapter 220, modem 222, read only memory (ROM) 224, hard disk drive (HDD) 226, CD-ROM drive 230, universal serial bus (USB) ports and other communication ports 232, and PCI/PCIe devices 234 connect to SB/ICH 204 through bus 238 and bus 240. PCI/PCIe devices may include, for example, Ethernet adapters, add-in cards, and PC cards for notebook computers. PCI uses a card bus controller, while PCIe does not. ROM 224 may be, for example, a flash basic input/output system (BIOS).

HDD 226 and CD-ROM drive 230 connect to SB/ICH 204 through bus 240. HDD 226 and CD-ROM drive 230 may use, for example, an integrated drive electronics (IDE) or serial advanced technology attachment (SATA) interface. Super I/O (SIO) device 236 is connected to SB/ICH 204.

An operating system runs on processing unit 206. The operating system coordinates and provides control of various components within the data processing system 200 in FIG. 2. As a client, the operating system is a commercially available operating system such as Microsoft® Windows 8®. An object-oriented programming system, such as the Java™ programming system, may run in conjunction with the operating system and provides calls to the operating system from Java™ programs or applications executing on data processing system 200.

As a server, data processing system 200 may be, for example, an IBM® eServer™ System p® computer system, running the Advanced Interactive Executive (AIX®) operating system or the LINUX® operating system. Data processing system 200 may be a symmetric multiprocessor (SMP) system including a plurality of processors in processing unit 206. Alternatively, a single processor system may be employed.

Instructions for the operating system, the object-oriented programming system, and applications or programs are located on storage devices, such as HDD 226, and are loaded into main memory 208 for execution by processing unit 206. The processes for illustrative embodiments of the present invention are performed by processing unit 206 using computer usable program code, which is located in a memory such as, for example, main memory 208, ROM 224, or in one or more peripheral devices 226 and 230, for example.

A bus system, such as bus 238 or bus 240 as shown in FIG. 2, is comprised of one or more buses. Of course, the bus system may be implemented using any type of communication fabric or architecture that provides for a transfer of data between different components or devices attached to the fabric or architecture. A communication unit, such as modem 222 or network adapter 212 of FIG. 2, includes one or more devices used to transmit and receive data. A memory may be, for example, main memory 208, ROM 224, or a cache such as found in NB/MCH 202 in FIG. 2.

Those of ordinary skill in the art will appreciate that the hardware depicted in FIGS. 1 and 2 may vary depending on the implementation. Other internal hardware or peripheral devices, such as flash memory, equivalent non-volatile memory, or optical disk drives and the like, may be used in addition to or in place of the hardware depicted in FIGS. 1 and 2. Also, the processes of the illustrative embodiments may be applied to a multiprocessor data processing system, other than the SMP system mentioned previously, without departing from the spirit and scope of the present invention.

Moreover, the data processing system 200 may take the form of any of a number of different data processing systems including client computing devices, server computing devices, a tablet computer, laptop computer, telephone or other communication device, a personal digital assistant (PDA), or the like. In some illustrative examples, data processing system 200 may be a portable computing device that is configured with flash memory to provide non-volatile memory for storing operating system files and/or user-generated data, for example. Essentially, data processing system 200 may be any known or later developed data processing system without architectural limitation.

FIG. 3 is an example diagram illustrating an interaction of elements of a healthcare cognitive system in accordance with one illustrative embodiment. The example diagram of FIG. 3 depicts an implementation of a healthcare cognitive system 300, which may be a healthcare cognitive system such as healthcare cognitive system 100 described in FIG. 1, that is configured to provide interactive information associated with a patient on a hospital garment worn by the patient and/or hospital staff. However, it should be appreciated that this is only an example implementation and other healthcare operations may be implemented in other embodiments of the healthcare cognitive system 300 without departing from the spirit and scope of the present invention.

Moreover, it should be appreciated that while FIG. 3 depicts the patient 302 and medical staff 306 as human figures, the interactions with and between these entities may be performed using computing devices, medical equipment, and/or the like, such that entities 302 and 306 may in fact be computing devices, e.g., client computing devices, such as radio-frequency identification (RFID), Indoor Positioning Sensing (IPS), or the like, signals received from the patient's and/or medical staff's garment, identification card, or the like. For example, the interactions 304, 306, 308, 314, and 316 from patient 302 and medical staff 306 may be performed orally, e.g., a doctor interviewing a patient, and may involve the use of one or more medical instruments, monitoring devices, or the like, to collect information that may be input to the healthcare cognitive system 300. Interactions between medical staff 306 and the healthcare cognitive system 300 may be electronic via a user computing device (not shown), such as a client computing device 110 or 112 in FIG. 1, communicating with the healthcare cognitive system 300 via one or more data communication links and potentially one or more data networks. Further, additional monitoring information may be input into healthcare cognitive system 300 from monitoring devices 340, such as scanners, location detectors, hospital garments worn by the patient and/or medical staff, inventory systems, or the like.

As shown in FIG. 3, in accordance with one illustrative embodiment, a patient 302, medical staff 306, and monitoring device 340 presents information to healthcare cognitive system 300 and, more specifically patient care analysis engine 320 within healthcare cognitive system 300. Patient care analysis engine 320 receives input such as but not limited to:

Biometric information associated with a patient.
Scanner, digital reader, or the like, that scans medication, medical devices, or the like, when being pulled from inventory in order to be administered to the patient.
Scanner, digital reader, or the like, that scans medication, medical devices, or the like, prior to being administered to the patient.
Location monitors that identify patient and medical staff location throughout the facility of which the patient is a visitor.
Information from the patient's electronic medical records (EMR) including, but not limited to, a patient's medical history, doctor's orders for the patient, or the like.
Medical information associated with diseases, drug interactions, or the like.

Upon receiving the input from the plurality of devices, input analysis logic 322 analyzes the input for key elements for use in identifying one or more questions to pose to a request processing pipeline implemented by healthcare cognitive system 300, which input analysis logic 322 identifies from search question database 328. The questions may be, for example, "Is Doctor [N] an attending doctor of patient [A]?", "Is it time for the blood pressure of patient [A] to be checked?", "Has patient [A] performed the scheduled physical therapy?", "Has patient [A], who is returning from a procedure, entered the correct patient room?", "Do the vital signs of patient [A] indicate that patient[A] is experiencing an issue?, or the like. Responsive to input analysis logic 322 identifying an existence of one or more questions from question database 328 that are associated with a provided input, input analysis logic 322 sends the one or more questions to the request processing pipeline implemented by healthcare cognitive system 300.

The request processing pipeline parses and interprets the question/request and provides a response to patient care analysis engine 320. That is, the request processing pipeline comprises a plurality of stages for processing an input question/request based on information gathered from medical corpus and other source data 336, treatment guidance data 334, and the patient EMRs 332 associated with the patient 302. The request processing pipeline 308 generates answers/responses for the input question or request based on the processing of the input question/request and medical corpus and other source data 336, treatment guidance data 334, and the patient EMRs 332 associated with the patient 302. Based on the application of the queries to medical corpus and other source data 336, treatment guidance data 334, and the patient EMRs 332 associated with the patient 302, a set of hypotheses, or candidate answers/responses to the input question/request, are generated by looking across medical corpus and other source data 336, treatment guidance data 334, and the patient EMRs 332 associated with the patient 302 for portions of the medical corpus and other source data 336, treatment guidance data 334, and the patient EMRs 332 associated with the patient 302 that have some potential for containing a valuable response to the input question/response (hereafter assumed to be an input question). The request processing pipeline then performs deep analysis on the language of the input question and the language used in each of the portions of medical corpus and other source data 336, treatment guidance data 334, and the patient EMRs 332 associated with the patient 302 found during the application of the queries using a variety of reasoning algorithms. The scores obtained from the various reasoning algorithms are then weighted against a statistical model that summarizes a level of confidence that the request processing pipeline has regarding the evidence that the potential candidate answer is inferred by the question. This process is be repeated for each of the candidate answers to generate ranked listing of candidate answers which may then be presented to patient care analysis engine 320.

Upon receiving the candidate answers from the request processing pipeline, response identification logic 324 utilizes the submitted question from input analysis logic 322 and the response from the request processing pipeline to identify an appropriate response to initiate from response signal database 330. For example, if the posed question is "Is it time for the blood pressure of patient [A] to be checked?" and the response is "No", then response identification logic 324 may identify that an appropriate response signal is to change a visual cue of all or a portion of the hospital garment worn by Patient A to a first color, such as green. Alternatively, if the posed question is "Is it time for the blood pressure of patient [A] to be checked?" and the response is "Yes", then response identification logic 324 may identify that an appropriate response signal is to change a visual cue of all or a portion of the hospital garment worn by Patient A to a second color, such as red. If two or more questions are posed to the request processing pipeline and if any of the answers indicate that a medical error may be cause by the administration of the medicine to Patient A, then response identification logic 324 may utilize the most negative signal as the signal to be initiated. For example, if the electronic medical records indicate that it is not time for the patient's blood pressure to be checked by the patient has not performed their physical therapy, then response identification logic 324 would use the patient not performing their physical therapy as an overriding factor and identify that an appropriate response signal is to change a visual cue of all or a portion of the hospital garment worn by Patient A to a first color, such as red.

Once response identification logic 324 has identified an appropriate signal to be sent to the hospital garment worn by Patient A, response identification logic 324 sends the identified signal to signal engine 326. Signal engine 326 then sends a communication as either response 310 and/or response 318 to one or more hospital garments associated with the patient and/or medical staff to indicate that a medical error may be forthcoming thereby causing the medical staff to verify the current procedure. For example, if a heart surgeon enters the room of a patient who is schedule for a knee replacement, patient care analysis engine 320 in association with the request processing pipeline identify that the doctor is in the wrong room thereby turning a visual cue of the hospital garment of the doctor to red. The change of a visual cue of the hospital garment would be an indication to the doctor that the doctor is in the wrong room.

Thus, the illustrative embodiments provide mechanisms for interactively indicating information associated with a patient on a hospital garment worn by the patient and/or hospital staff using a cognitively integrated system. The illustrative embodiments help solve the problem of medical errors by introducing interactive display capability to hospital garments. Integrated with a backend host and through obvious visual cues—such as changing colors and patterns—the hospital garments will ensure that the right patient is getting the right medical procedure or medicine at the right time, and that a doctor, surgeon, nurse, or other hospital staff is in the right place at the right time as well.

The present invention may be a system, a method, and/or a computer program product. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Java, Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/ or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

Figure 4:
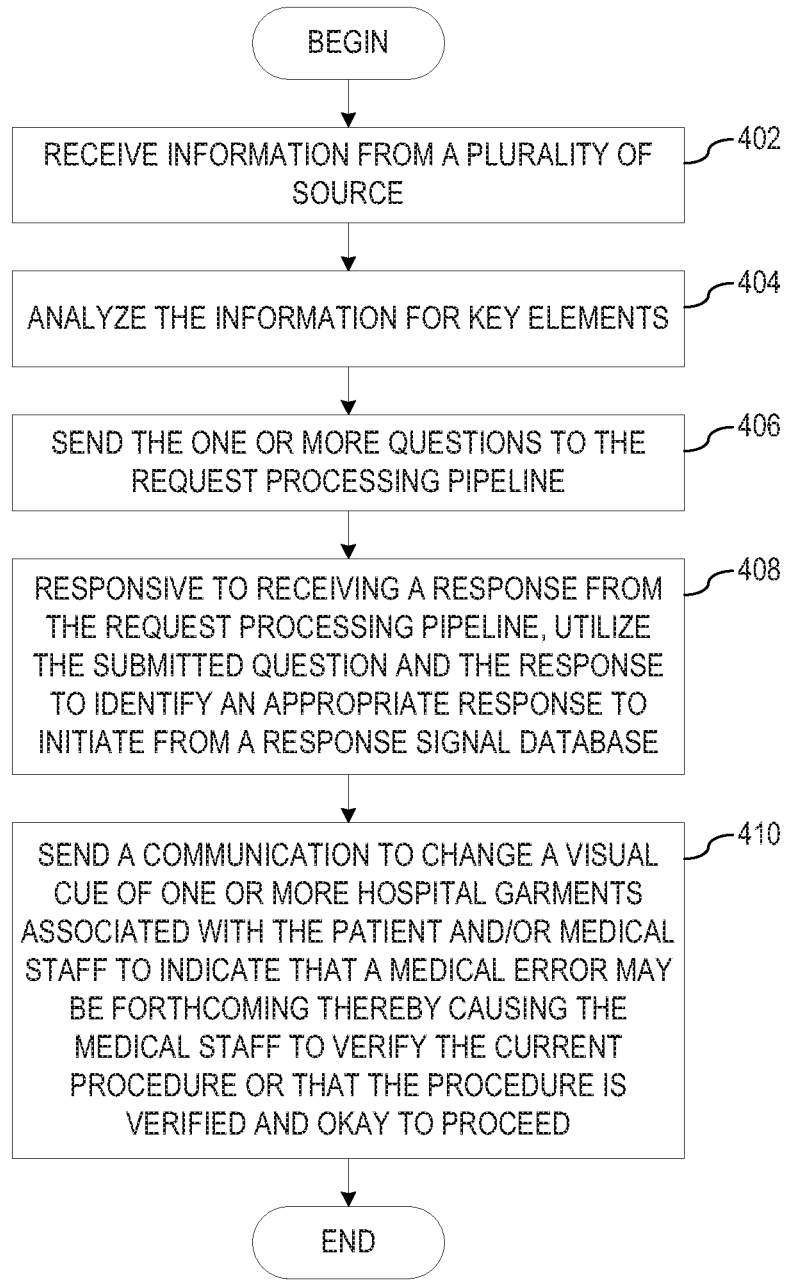
FIG. 4 is a flowchart outlining an example operation for interactively indicating information associated with a patient on a hospital garment worn by the patient and/or hospital staff using a cognitively integrated system in accordance with one illustrative embodiment.

FIG. 4 is a flowchart outlining an example operation for interactively indicating information associated with a patient on a hospital garment worn by the patient and/or hospital staff using a cognitively integrated system in accordance with one illustrative embodiment. The operation outlined in FIG. 4 may be implemented, for example, by a patient care analysis engine implemented in association with a healthcare cognitive system in one or more computing devices, such as patient care analysis engine 120 in FIG. 1 or patient care analysis engine 320 in FIG. 3, for example.

As the operation begins, a patient care analysis engine receives information from a plurality of sources (step 402), such as a patient, medical staff, monitoring devices, databases, or the like. The information may be provided via computing devices, medical equipment, scanners, location detectors, hospital garments worn by the patient and/or medical staff, inventory systems, or the like. The information may be but is not limited to:

Biometric information associated with a patient.
Scanner, digital reader, or the like, that scans medication, medical devices, or the like, when being pulled from inventory in order to be administered to the patient.
Scanner, digital reader, or the like, that scans medication, medical devices, or the like, prior to being administered to the patient.
Location monitors that identify patient and medical staff location throughout the facility of which the patient is a visitor.
Information from the patient's electronic medical records (EMR) including, but not limited to, a patient's medical history, doctor's orders for the patient, or the like.
Medical information associated with diseases, drug interactions, or the like.

Upon receiving the information from the plurality of sources, the patient care analysis engine analyzes the information for key elements (step 404) for use in identifying one or more questions from a search question database to pose to a request processing pipeline implemented by the healthcare cognitive system. Responsive to identifying an existence of one or more questions from the search question database that are associated with a provided input, the patient care analysis engine sends the one or more questions to the request processing pipeline (step 406). Responsive to receiving a response from the request processing pipeline, the patient care analysis engine utilizes the submitted question and the response to identify an appropriate response to initiate from a response signal database (step 408). Once the patient care analysis engine has identified an appropriate signal to be sent, the patient care analysis engine sends a communication to change a visual cue of one or more hospital garments associated with the patient and/or medical staff (step 410) to indicate that a medical error may be forthcoming thereby causing the medical staff to verify the current procedure or that the procedure is verified and okay to proceed. The operation terminates thereafter.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

Thus, the illustrative embodiments provide mechanisms for interactively indicating information associated with a patient on a hospital garment worn by the patient and/or hospital staff using a cognitively integrated system. The illustrative embodiments help solve the problem of medical errors by introducing interactive display capability to hospital garments. Integrated with a backend host and through obvious visual cues—such as changing colors and patterns—the hospital garments will ensure that the right patient is getting the right medical procedure or medicine at the right time, and that a doctor, surgeon, nurse, or other hospital staff is in the right place at the right time as well.

As noted above, it should be appreciated that the illustrative embodiments may take the form of an entirely hardware embodiment, an entirely software embodiment or an embodiment containing both hardware and software elements. In one example embodiment, the mechanisms of the illustrative embodiments are implemented in software or program code, which includes but is not limited to firmware, resident software, microcode, etc.

A data processing system suitable for storing and/or executing program code will include at least one processor coupled directly or indirectly to memory elements through a communication bus, such as a system bus, for example. The memory elements can include local memory employed during actual execution of the program code, bulk storage, and cache memories which provide temporary storage of at least some program code in order to reduce the number of times code must be retrieved from bulk storage during execution. The memory may be of various types including, but not limited to, ROM, PROM, EPROM, EEPROM, DRAM, SRAM, Flash memory, solid state memory, and the like.

Input/output or I/O devices (including but not limited to keyboards, displays, pointing devices, etc.) can be coupled to the system either directly or through intervening wired or wireless I/O interfaces and/or controllers, or the like. I/O devices may take many different forms other than conventional keyboards, displays, pointing devices, and the like, such as for example communication devices coupled through wired or wireless connections including, but not limited to, smart phones, tablet computers, touch screen devices, voice recognition devices, and the like. Any known or later developed I/O device is intended to be within the scope of the illustrative embodiments.

Network adapters may also be coupled to the system to enable the data processing system to become coupled to other data processing systems or remote printers or storage devices through intervening private or public networks. Modems, cable modems and Ethernet cards are just a few of the currently available types of network adapters for wired communications. Wireless communication based network adapters may also be utilized including, but not limited to, 802.11 a/b/g/n wireless communication adapters, Bluetooth wireless adapters, and the like. Any known or later developed network adapters are intended to be within the spirit and scope of the present invention.

The description of the present invention has been presented for purposes of illustration and description, and is not intended to be exhaustive or limited to the invention in the form disclosed. Many modifications and variations will be apparent to those of ordinary skill in the art without departing from the scope and spirit of the described embodiments. The embodiment was chosen and described in order to best explain the principles of the invention, the practical application, and to enable others of ordinary skill in the art to understand the invention for various embodiments with various modifications as are suited to the particular use contemplated. The terminology used herein was chosen to best explain the principles of the embodiments, the practical application or technical improvement over technologies found in the marketplace, or to enable others of ordinary skill in the art to understand the embodiments disclosed herein.

What is claimed is:

1. A method, in a data processing system, for interactively indicating information associated with a patient on a hospital garment, the method comprising:
    identifying a set of questions utilizing a set of information received from a plurality of sources within a medical facility;
    analyzing the set of information for a set of key elements;
    utilizing the set of key elements to identify one or more questions from a search question database;
    submitting the one or more questions to a request processing pipeline implemented by a healthcare cognitive system;
    responsive to receiving a response from the request processing pipeline, identifying one or more communications to be sent to one or more hospital garments associated with the patient and/or medical staff; and
    sending the one or more communications to the one or more hospital garments to cause the one or more hospital garments to change a visual cue.

2. The method of claim 1, wherein the one or more hospital garments are associated with the patient.

3. The method of claim 1, wherein the one or more hospital garments are associated with an individual on a medical staff of the medical facility.

4. The method of claim 1, wherein the one or more hospital garments displaying the color indicate that a medical error is forthcoming thereby causing a medical staff of the medical facility to verify a current procedure.

5. The method of claim 1, wherein the one or more hospital garments displaying the color indicate that a current procedure is verified and okay to proceed with.

6. The method of claim 1, wherein the plurality of sources include one or more of: a patient, medical staff, monitoring devices, or databases.

7. The method of claim 1, wherein the set of information includes one or more of:
    biometric information associated with a patient,
    a scan of medication or medical devices when being pulled from inventory in order to be administered to the patient,
    a scan of the medication or the medical devices prior to being administered to the patient,
    a location of a patient or medical staff location throughout the medical facility of which the patient is a visitor,
    information from the patient's electronic medical records (EMR), or
    medical information.

8. A computer program product comprising a non-transitory computer readable storage medium having a computer readable program stored therein, wherein the computer readable program, when executed on a computing device, causes the computing device to:
    identify a set of questions utilizing a set of information received from a plurality of sources within a medical facility;
    analyze the set of information for a set of key elements;
    utilize the set of key elements to identify one or more questions from a search question database;
    submit the one or more questions to a request processing pipeline implemented by a healthcare cognitive system;
    responsive to receiving a response from the request processing pipeline, identify one or more communications to be sent to one or more hospital garments associated with the patient and/or medical staff; and
    send the one or more communications to the one or more hospital garments to cause the one or more hospital garments to change a visual cue.

9. The computer program product of claim 8, wherein the one or more hospital garments are associated with the patient.

10. The computer program product of claim 8, wherein the one or more hospital garments are associated with an individual on a medical staff of the medical facility.

11. The computer program product of claim 8, wherein the one or more hospital garments displaying the color indicate that a medical error is forthcoming thereby causing a medical staff of the medical facility to verify a current procedure.

12. The computer program product of claim 8, wherein the one or more hospital garments displaying the color indicate that a current procedure is verified and okay to proceed with.

13. The computer program product of claim 8, wherein the plurality of sources include one or more of: a patient, medical staff, monitoring devices, or databases.

14. The computer program product of claim 8, wherein the set of information includes one or more of:
    biometric information associated with a patient,
    a scan of medication or medical devices when being pulled from inventory in order to be administered to the patient,
    a scan of the medication or the medical devices prior to being administered to the patient,
    a location of a patient or medical staff location throughout the medical facility of which the patient is a visitor,
    information from the patient's electronic medical records (EMR), or
    medical information.

15. An apparatus comprising:

a processor; and a memory coupled to the processor, wherein the memory comprises instructions which, when executed by the processor, cause the processor to:

identify a set of questions utilizing a set of information received from a plurality of sources within a medical facility;

analyze the set of information for a set of key elements;

utilize the set of key elements to identify one or more questions from a search question database;

submit the one or more questions to a request processing pipeline implemented by a healthcare cognitive system;

responsive to receiving a response from the request processing pipeline, identify one or more communications to be sent to one or more hospital garments associated with the patient and/or medical staff; and send the one or more communications to the one or more hospital garments to cause the one or more hospital garments to change a visual cue.

16. The apparatus of claim 15, wherein the one or more hospital garments are associated with the patient.

17. The apparatus of claim 15, wherein the one or more hospital garments are associated with an individual on a medical staff of the medical facility.

18. The apparatus of claim 15, wherein the one or more hospital garments displaying the color indicate that a medical error is forthcoming thereby causing a medical staff of the medical facility to verify a current procedure.

19. The apparatus of claim 15, wherein the one or more hospital garments displaying the color indicate that a current procedure is verified and okay to proceed with.

20. The apparatus of claim 15, wherein the plurality of sources include one or more of: a patient, medical staff, monitoring devices, or databases.

* * * * *